United States Patent
Tsuruno et al.

(10) Patent No.: US 12,210,014 B2
(45) Date of Patent: Jan. 28, 2025

(54) METHOD FOR DETECTING TARGET SUBSTANCE, REAGENT FOR DETECTING TARGET SUBSTANCE

(71) Applicant: SYSMEX CORPORATION, Kobe (JP)

(72) Inventors: Chikayuki Tsuruno, Kobe (JP); Takuya Kyoutou, Kobe (JP); Tadashi Ishimoto, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 763 days.

(21) Appl. No.: 17/459,158

(22) Filed: Aug. 27, 2021

(65) Prior Publication Data

US 2021/0389312 A1 Dec. 16, 2021

Related U.S. Application Data (63) Continuation of application No. PCT/JP2020/008328, filed on Feb. 28, 2020.

(30) Foreign Application Priority Data

Feb. 28, 2019 (JP) ................................ 2019-035529

(51) Int. Cl.
*G01N 33/543* (2006.01)

(52) U.S. Cl.
CPC .......... *G01N 33/54306* (2013.01); *G01N 2333/4725* (2013.01); *G01N 2400/02* (2013.01); *G01N 2440/38* (2013.01)

(58) Field of Classification Search
CPC ..... G01N 33/54306; G01N 2333/4725; G01N 2400/02; G01N 2440/38; G01N 2333/42;
(Continued)

(56) References Cited

U.S. PATENT DOCUMENTS

2011/0171662 A1* 7/2011 Grenier .............. G01N 33/5306 435/7.1
2012/0190576 A1* 7/2012 Narimatsu ....... G01N 33/57469 530/395
(Continued)

FOREIGN PATENT DOCUMENTS

| CN | 105424942 A | 3/2016 |
|---|---|---|
| CN | 106030305 A | 10/2016 |
| CN | 108351359 A | 7/2018 |
| WO | 2015/129384 A1 | 9/2015 |
| WO | 2015/194350 A1 | 12/2015 |

OTHER PUBLICATIONS

Guesdon JL, Avrameas S. Lectin immuno tests: quantitation and titration of antigens and antibodies using lectin-antibody conjugates. J Immunol Methods. 1980;39(1-2):1-13. (Year: 1980).*

(Continued)

*Primary Examiner* — Christopher L Chin
*Assistant Examiner* — Christina Lusi
(74) *Attorney, Agent, or Firm* — Sughrue Mion, PLLC (57) ABSTRACT

Disclosed is a method for detecting a target substance, comprising: forming on a carrier a complex comprising *Wisteria floribunda* lectin (WFA) and a target substance by mixing the WFA immobilized on the carrier with the target substance comprising a sugar chain that binds to the WFA in the presence of an alcohol having 1 to 7 carbon atoms consisting of carbon atoms, hydrogen atoms, and oxygen atoms; and detecting the target substance by detecting the complex.

9 Claims, 6 Drawing Sheets

(58) Field of Classification Search
CPC ............. G01N 33/5306; G01N 33/533; G01N 33/535; G01N 33/543; G01N 33/54313; G01N 33/54326
USPC .................................. 435/7.1, 7.8; 436/501
See application file for complete search history.

(56) References Cited

U.S. PATENT DOCUMENTS

| | | |
|---|---|---|
| 2015/0309019 A1 | 10/2015 | Kaneko et al. |
| 2016/0363586 A1 | 12/2016 | Tsuruno et al. |
| 2017/0122940 A1 | 5/2017 | Kaneko et al. |
| 2020/0048723 A1* | 2/2020 | Yamashita ......... G01N 33/5308 |

OTHER PUBLICATIONS

Extended European search report issued on Feb. 14, 2023 in a counterpart European patent application No. 20763781.0.

Japanese Office Action issued on Nov. 7, 2023 in a counterpart Japanese patent application No. 2021-502397.

M. Luísa S. Silva: "Lectin-based biosensors as analytical tools for clinical oncology", Cancer Letters, 2018, vol. 436, pp. 63-74, Elsevier B.V.

Communication pursuant to Rule 164(1) EPC and Partial Supplementary European Search Report issued on Nov. 14, 2022 in a counterpart European patent application No. 20763781.0.

Atsushi Kuno et al., "A serum "sweet-doughnut" protein facilitates fibrosis evaluation and therapy assessment in patients with viral hepatitis", Scientific Reports, Jan. 15, 2013, pp. 1-9, vol. 3, Article No. 1065.

Etsuko Iio et al., "A novel glycobiomarker: Wisteria floribunda agglutinin+-Mac-2 binding protein, M2BPGi, for predicting liver fibrosis", Modern Media, Feb. 2016, pp. 15-20, vol. 62, No. 2.

International Search Report ("ISR") mailed on Jun. 2, 2020 for PCT/JP2020/008328.

Written Opinion("WO") mailed on Jun. 2, 2020 for PCT/JP2020/008328.

Chinese Office Action issued on Mar. 13, 2024 in a counterpart Chinese patent application No. 202080016523.9.

* cited by examiner

METHOD FOR DETECTING TARGET SUBSTANCE, REAGENT FOR DETECTING TARGET SUBSTANCE

CROSS REFERENCE TO RELATED APPLICATIONS

This is a Continuation of International Application No. PCT/JP2020/008328, filed on Feb. 28, 2020, and this application claims priority from prior Japanese Patent Application No. 2019-035529, filed on Feb. 28, 2019, entitled "METHOD FOR DETECTING TARGET SUBSTANCE, REAGENT FOR DETECTING TARGET SUBSTANCE, AND REAGENT KIT FOR DETECTING TARGET SUBSTANCE", the entire contents of which are incorporated herein by reference.

FIELD OF THE INVENTION

The present invention relates to a method for detecting a target substance.

BACKGROUND

US 2017/0,122,940 A discloses a sandwich type assay for quantifying a glycoprotein as a substance to be detected in a specimen using a labeled lectin, in which influence derived from impurities is suppressed by introducing a simple treatment.

SUMMARY OF THE INVENTION

The scope of the present invention is defined solely by the appended claims, and is not affected to any degree by the statements within this summary.

US 2017/0,122,940 A describes a method for suppressing non-specific binding of a labeled lectin using a reducing agent such as thioglycerol. However, the inventors have found that the method described in US 2017/0,122,940 A does not sufficiently improve detection accuracy as shown in Examples described later.

One embodiment of the present invention relates to a method for detecting a target substance, comprising: forming on a carrier a complex comprising *Wisteria floribunda* lectin (WFA) and a target substance by mixing the WFA immobilized on the carrier with the target substance comprising a sugar chain that binds to the WFA in the presence of an alcohol having 1 to 7 carbon atoms consisting of carbon atoms, hydrogen atoms, and oxygen atoms; and detecting the target substance by detecting the complex.

One embodiment of the present invention relates to a method for detecting a target substance, comprising: forming on a carrier a complex comprising *Wisteria floribunda* lectin (WFA) and a target substance by mixing the WFA immobilized on the carrier with the target substance comprising a sugar chain that binds to the WFA in the presence of an alcohol having 1 to 7 carbon atoms (excluding thioglycerol); and detecting the target substance by detecting the complex.

One embodiment of the present invention relates to a method for detecting a target substance, comprising: forming on a carrier a complex comprising *Wisteria floribunda* lectin (WFA) and a target substance by mixing the WFA immobilized on the carrier with the target substance comprising a sugar chain that binds to the WFA in the presence of an alcohol having 1 to 7 carbon atoms (excluding alcohols comprising a thiol group); and detecting the target substance by detecting the complex.

DETAILED DESCRIPTION OF THE PREFERRED EMBODIMENTS

1. Detection Method

An example of an embodiment of a detection method disclosed herein is shown. One embodiment of the present disclosure relates to a method for detecting a target substance, comprising forming on a carrier a complex comprising WFA and a target substance by mixing lectin with the target substance comprising a sugar chain that binds to the lectin in the presence of an alcohol (formation step); and detecting the target substance by detecting the complex (detection step). Preferably, the detection may be quantitative.

The target substance is a substance to be detected. The target substance is preferably a glycoprotein, and more preferably has a sugar chain that binds to *Wisteria floribunda* lectin (WFA). Preferable examples of the target substance include Mac-2-binding protein (M2BP), Mucin 1, cell surface associated (MUC1), α1 acid glycoprotein (AGP), nerve cell adhesion molecule L1 (L1CAM), KL-6 antigen, and the like.

The target substance is preferably a substance contained in a sample collected from a living body. As the sample, urine and blood can be used. The blood may be peripheral blood, or plasma or serum prepared from the peripheral blood. Among them, plasma or serum is preferable.

In the present embodiment, the sample may be diluted with an appropriate aqueous medium, as necessary. Such an aqueous medium is not particularly limited as long as it does not interfere with detection of the target substance, and examples thereof include water, physiological saline, a buffer solution, and the like. The buffer solution is not particularly limited, and a buffer solution at a pH near neutrality (for example, a pH of 6 or more and 8 or less) can be used. Examples thereof include Good's buffers such as HEPES, MES, Tris and PIPES, phosphate buffered saline (PBS), and the like.

Preferable examples of the lectin include WFA. Examples of the WFA include naturally occurring WFA or recombinant WFA. Naturally occurring WFA is a tetrameric protein including four subunits. WFA is known as a lectin contained in seeds of *Wisteria floribunda*. From this tetrameric WFA, a monomer or dimeric WFA can be obtained by a predetermined treatment using a reducing agent or the like. In the present specification, unless otherwise specified, the notation "WFA" intends both monomeric WFA and multimeric WFA. In addition, in the present specification, when referring to WFA including a predetermined number of subunits, for example, as in "monomeric WFA", "dimeric WFA" and "tetrameric WFA", the number of subunits is clearly written.

In the present embodiment, the WFA may be a tetrameric WFA, or may be a monomeric WFA or a dimeric WFA. Among them, a dimeric WFA is preferable from the point of high reactivity.

Examples of the alcohol include alcohols having 1 to 7 carbon atoms, preferably 2 to 7 carbon atoms. The lower limit of the number of carbon atoms of the alcohol can be selected from 1, 2, or 3. In one embodiment, an alcohol consisting of carbon atoms, hydrogen atoms and oxygen atoms is used. Preferably, the alcohol having 1 to 7 carbon atoms does not comprise thioglycerol. More preferably, the alcohol having 1 to 7 carbon atoms does not comprise an alcohol comprising a thiol group. Here, the phrase "the alcohol having 1 to 7 carbon atoms does not comprise thioglycerol" means that it is sufficient to comprise at least an alcohol having 1 to 7 carbon atoms other than thioglycerol in the detection system, reagent, and reagent kit described later, and does not completely exclude a detection system, reagent, and reagent kit to which thioglycerol is added. The expression of "the alcohol having 1 to 7 carbon atoms does not comprise an alcohol comprising a thiol group" also means that it is sufficient to comprise at least an alcohol having 1 to 7 carbon atoms other than an alcohol comprising a thiol group in the detection system, reagent, and reagent kit described later, and does not completely exclude a detection system, reagent, and reagent kit to which an alcohol comprising a thiol group is added. That is, thioglycerol may be contained to such an extent that it does not interfere with detection of the target substance.

The alcohol may be monovalent or polyvalent. The valence intends the number of hydroxyl groups. Examples of the polyhydric alcohol include dihydric, trihydric, and tetrahydric alcohols.

The carbon chain contained in the alcohol may be linear or branched, but is preferably linear.

As the alcohol, only one kind or a plurality of kinds may be used.

Examples of the alcohol preferably include at least one alcohol selected from the group consisting of methanol, ethanol, glycerol, pentanol, heptanol, diglycerol, ethylene glycol, diethylene glycol, propylene glycol, dipropylene glycol, triethylene glycol, and mixtures thereof. At least one alcohol selected from the group consisting of glycerol, diglycerol, ethylene glycol, diethylene glycol, propylene glycol, dipropylene glycol, triethylene glycol, and mixtures thereof is more preferable, and glycerol is most preferable.

The formation of a complex of WFA and a target substance is achieved by, for example, mixing a sample comprising the target substance (or a diluent obtained by diluting the sample with an aqueous medium or the like) with WFA and incubating the mixture for a certain period of time as necessary. In this case, the WFA is preferably immobilized on the carrier.

The mode of immobilization of the WFA on the carrier is not particularly limited. For example, the WFA and the carrier may be bound directly, or the WFA and the carrier may be bound indirectly via another substance. Examples of the direct binding include physical adsorption and the like. Examples of the indirect bond include a bond via a combination of biotin and avidin or streptavidin (hereinafter also referred to as "avidins"). In this case, by preliminarily modifying the WFA with biotin and previously binding avidins to the carrier, the WFA and the carrier can be bound indirectly via the binding between biotin and avidins.

The material of the carrier is not particularly limited. For example, the material can be selected from organic polymer compounds, inorganic compounds, biopolymers, and the like. Examples of the organic polymer compound include latex, polystyrene, polypropylene, and the like. Examples of the inorganic compound include magnetic bodies (iron oxide, chromium oxide, ferrite, and the like), silica, alumina, glass, and the like. Examples of the biopolymer include insoluble agarose, insoluble dextran, gelatin, cellulose, and the like. Two or more of these may be used in combination. The shape of the carrier is not particularly limited, and examples thereof include particles, membranes, microplates, microtubes, test tubes, and the like. Among them, particles are preferable, and magnetic particles are particularly preferable. By using the magnetic particles, reactivity between the WFA and the target substance can be improved.

The WFA to be immobilized on the magnetic particles is preferably a dimeric WFA. The dimeric WFA can be obtained, for example, by dissociating subunits of a tetrameric WFA using a sulfhydryl reagent or a reducing agent. Also, by bringing a crosslinking agent into contact with a tetrameric WFA, the tetrameric WFA can be dimerized. As such a crosslinking agent, a crosslinking agent that forms a crosslink with the amino group in the tetrameric WFA is preferable. Examples of the crosslinking agent having a reactive group for the amino group include crosslinking agents having at least one functional group selected from the group consisting of an N-hydroxysuccinimide ester group, an isothiocyano group, a chlorosulfone group, a chlorocarbonyl group, an oxyethylene group, a chloroalkyl group having 1 to 4 carbon atoms, an aldehyde group and a carboxyl group. By using such a crosslinking agent, the tetrameric WFA can be efficiently dimerized.

The molar ratio (WFA/crosslinking agent) when mixing the tetrameric WFA and the crosslinking agent is preferably 1/10 or less, and more preferably 1/20 or less. On the other hand, the lower limit of the molar ratio (WFA/crosslinking agent) can be set to 1/100 or more, in consideration of the balance between the amount of the crosslinking agent used and the yield of the dimeric WFA to be produced.

In the case where the WFA is immobilized on magnetic particles through the binding between biotin and avidins, biotinylated dimeric WFA may be used. The biotinylated dimeric WFA can be obtained, for example, by dimerizing tetrameric WFA using a crosslinking agent comprising biotin. The crosslinking agent comprising biotin can be obtained, for example, by binding biotin and the reactive group of the crosslinking agent through a spacer. Such a spacer is not particularly limited, but examples thereof include compounds having an aminohexanoyl group (aminocaproyl group) and the like.

When forming a complex of a target substance and WFA, the alcohol is contained in an amount of 2 to 20 w/w %, preferably 4 to 10 w/w %. In the present disclosure, the unit "w/w %" intends a percentage in terms of weight/weight (the same applies hereinafter).

When a complex of a target substance and WFA is formed in the presence of alcohol, a reagent comprising alcohol and a reagent comprising WFA immobilized on the carrier as individual reagents may be mixed with a sample (or a diluent thereof), or a mixed solution of alcohol and WFA immobilized on the carrier may be mixed with a sample. The order of mixing the reagents and the sample (or the diluent thereof) is not particularly limited, and these may be mixed substantially simultaneously or sequentially mixed. Examples of the reagent comprising alcohol include a reagent obtained by adding alcohol to a HISCL (trademark) R1 reagent manufactured by Sysmex Corporation. In this case, examples of the reagent comprising WFA immobilized on the carrier include a HISCL (trademark) M2BPGi (trademark) R2 reagent manufactured by Sysmex Corporation.

The detection of the complex becomes possible, for example, by further comprising a detection substance in the complex of the WFA and the target substance and detecting a signal from the detection substance. The complex of the WFA, the target substance and the detection substance can be formed by mixing the complex of the WFA and the target substance with the detection substance and reacting them for a certain period of time as necessary. In addition, a complex of the WFA, the target substance, and the detection substance may be formed by allowing the detection substance to coexist at the time of forming the complex of the WFA and the target substance.

The detection substance is a substance that specifically binds to the target substance, and is not limited as long as it is a substance comprising a labeling substance. When the target substance is a glycoprotein, the substance that specifically binds to the target substance preferably binds to a protein portion of the target substance. Examples of the substance that specifically binds to the target substance include antibodies. The antibody may be any of monoclonal antibodies, polyclonal antibodies, and fragments thereof (for example, Fab, F(ab')2, etc.). Alternatively, a commercially available antibody may be used.

As the labeling substance used for the detection substance, a substance usually used in the art in immunological measurement can be used. For example, it may be a substance which itself generates a signal (hereinafter also referred to as "signal generating substance") or a substance which catalyzes the reaction of other substances to generate a signal. Examples of the signal generating substance include fluorescent substances, radioactive isotopes, and the like. Examples of the substance that catalyzes the reaction of other substances to generate a detectable signal include enzymes. Examples of the enzymes include alkaline phosphatase, peroxidase, β-galactosidase, luciferase, and the like. Examples of the fluorescent substances include fluorescent dyes such as fluorescein isothiocyanate (FITC), rhodamine and Alexa Fluor (trademark), fluorescent proteins such as GFP, and the like. Examples of the radioactive isotopes include $^{125}I$ $^{14}C$, $^{32}P$, and the like. Among them, an enzyme is preferable as a labeling substance, and alkaline phosphatase is particularly preferable. A hapten such as a dinitrophenyl (DNP) group or biotin can also be used as the labeling substance. By binding a substance that binds to a hapten and has a signal generating substance, an enzyme or the like to a detection substance, a signal from the complex can be acquired.

The labeling substance can be bound to a substance that specifically binds to the target substance by a labeling method known in the art. Labeling may also be performed using a commercially available labeling kit or the like.

In the present embodiment, the complex is detected based on the labeling substance of the detection substance contained in the complex. Specifically, a measured value reflecting the amount or concentration of the labeling substance contained in the sample can be obtained by detecting a signal generated by the labeling substance of the detection substance contained in the complex. The phrase "detecting a signal" herein includes qualitatively detecting the presence or absence of a signal, quantifying a signal intensity, and semi-quantitatively detecting the intensity of a signal. Semi-quantitative detection means to show the intensity of the signal in stages like "no signal generated", "weak", "medium", "strong", and the like. In the present embodiment, it is preferable to detect the intensity of a signal quantitatively or semi-quantitatively.

Methods for detecting a signal themselves are known in the art. In the present embodiment, a measurement method according to the type of signal derived from the labeling substance may be appropriately selected. For example, when the labeling substance is an enzyme, signals such as light and color generated by reacting a substrate for the enzyme can be measured by using a known apparatus such as a spectrophotometer.

The substrate of the enzyme can be appropriately selected from known substrates according to the type of the enzyme. For example, when alkaline phosphatase is used as the enzyme, examples of the substrate include chemiluminescent substrates such as CDP-Star (trademark) (disodium 4-chloro-3-(methoxyspiro[1,2-dioxetane-3,2'-(5'-chloro)tricyclo[3.3.1.13,7]decan]-4-yl)phenyl phosphate) and CSPD (trademark) (disodium 3-(4-methoxyspiro[1,2-dioxetane-3,2-(5'-chloro)tricyclo[3.3.1.13,7]decan]-4-yl)phenyl phosphate), and chromogenic substrates such as 5-bromo-4-chloro-3-indolyl phosphate (BCIP), disodium 5-bromo-6-chloro-indolyl phosphate, and p-nitrophenyl phosphate.

When the labeling substance is a radioactive isotope, radiation as a signal can be measured using a known apparatus such as a scintillation counter. Also, when the labeling substance is a fluorescent substance, fluorescence as a signal can be measured using a known apparatus such as a fluorescence microplate reader. The excitation wavelength and the fluorescence wavelength can be appropriately determined according to the type of fluorescent substance used.

Examples of the reagent comprising the detection substance, for example, when the target substance is M2BP, include a HISCL (trademark) M2BPGi (trademark) R3 reagent manufactured by Sysmex Corporation. Also, when detecting another target substance, an anti-M2BP antibody contained in the HISCL (trademark) M2BPGi (trademark) R3 reagent can be changed according to the substance that specifically binds to the target substance.

In the present embodiment, when the labeling substance is an enzyme, a step of bringing a substrate into contact with the labeling substance and a step of detecting a signal are referred to as "detection step". Also, when the labeling substance is a fluorescent substance or a radioisotope, a step of detecting a signal is referred to as "detection step".

In the present embodiment, Bound/Free (B/F) separation for removing an unreacted free component not forming a complex may be performed between the formation of the complex and the detection step. The unreacted free component refers to a component not constituting a complex. Examples thereof include unreacted sample components, WFA, detection substance, and the like. The means of B/F separation is not particularly limited, and when the carrier is a particle, B/F separation can be performed by recovering only the carrier capturing the complex by centrifugation. When the carrier is a container such as a microplate or a microtube, B/F separation can be performed by removing a liquid comprising an unreacted free component. When the carrier is a magnetic particle, B/F separation can be performed by aspirating and removing a liquid comprising an unreacted free component by a nozzle while magnetically constraining the magnetic particles with a magnet, which is preferable from the viewpoint of automation. After removing the unreacted free component, the carrier capturing the complex may be washed with a suitable aqueous medium such as PBS.

The detection result of the signal can be used as the measured value of target substance. For example, when quantitatively detecting the intensity of a signal, the measured value itself of the signal intensity or the value calculated from the measured value can be used as the measured value of target substance. Examples of the value calculated from the measured value of the signal intensity include a value obtained by subtracting the measured value of the negative control sample from the measured value, a value obtained by dividing the measured value by the measured value of the positive control sample, combinations thereof, and the like.

Here, the detection of the target substance may be performed using a fully automated immunoassay system HISCL (trademark) series manufactured by Sysmex Corporation.

2. Reagent and Reagent Kit
(1) Reagent

Figure 1A:
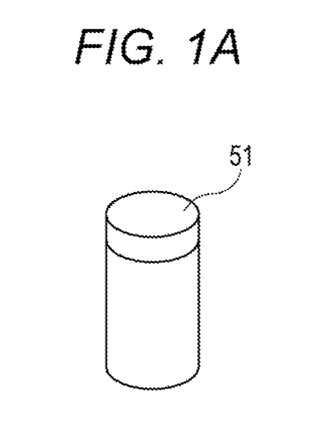
FIG. 1A is a view showing an appearance example of a container comprising a reagent.

One embodiment of the present disclosure relates to a reagent used in the detection of the target substance. Preferably, the present embodiment includes a reagent comprising an alcohol having 1 to 7 carbon atoms used in some steps of the method described in the above 1. FIG. 1(A) shows an appearance of a container 51 of reagent.

It is preferable that the reagent comprises 3 to 30 w/w %, preferably 4 to 15 w/w % of an alcohol having 1 to 7 carbon atoms. Also, it is preferable that the reagent 51 comprises, for example, an aqueous solvent. The aqueous solvent is not particularly limited as long as it does not interfere with the detection described in the above 1, and examples thereof include water, physiological saline, a buffer solution, and the like. The buffer solution is not particularly limited as long as it has a buffering effect at a pH near neutrality (for example, a pH of 6 or more and 8 or less). Examples of the buffer solution include Good buffers such as HEPES, MES, Tris and PIPES, phosphate buffered saline (PBS), and the like. The buffer solution is preferably HEPES. Examples of such a buffer solution include a HISCL (trademark) R1 reagent manufactured by Sysmex Corporation.

In addition, the reagent comprising an alcohol having 1 to 7 carbon atoms may comprise WFA immobilized on the carrier described in the above 1. Also in this case, it is preferable that the reagent comprises, for example, an aqueous solvent. The aqueous solvent is not particularly limited as long as it does not interfere with the detection described in the above 1, and examples thereof include water, physiological saline, a buffer solution, and the like. The buffer solution is not particularly limited as long as it has a buffering effect at a pH near neutrality (for example, a pH of 6 or more and 8 or less). Examples of the buffer solution include Good buffers such as HEPES, MES, Tris and PIPES, phosphate buffered saline (PBS), and the like. The buffer solution is preferably HEPES. Examples of such a buffer solution include a HISCL (trademark) M2BPGi (trademark) R2 reagent manufactured by Sysmex Corporation.

Furthermore, the reagent may comprise the detection substance described in the above 1.

The reagent may comprise at least one additive selected from stabilizers such as β-mercaptoethanol and DTT; protective agents such as albumin; surfactants such as polyoxyethylene sorbitan monooleate, polyoxyethylene(20) sorbitan monolaurate, and polyoxyethylene(10) octylphenyl ether; and stabilizers such as sodium azide and bovine serum albumin. The reagent may comprise a metal salt (preferably a chloride) of sodium, potassium, calcium, or manganese.

(2) Reagent Kit

Figure 1B:
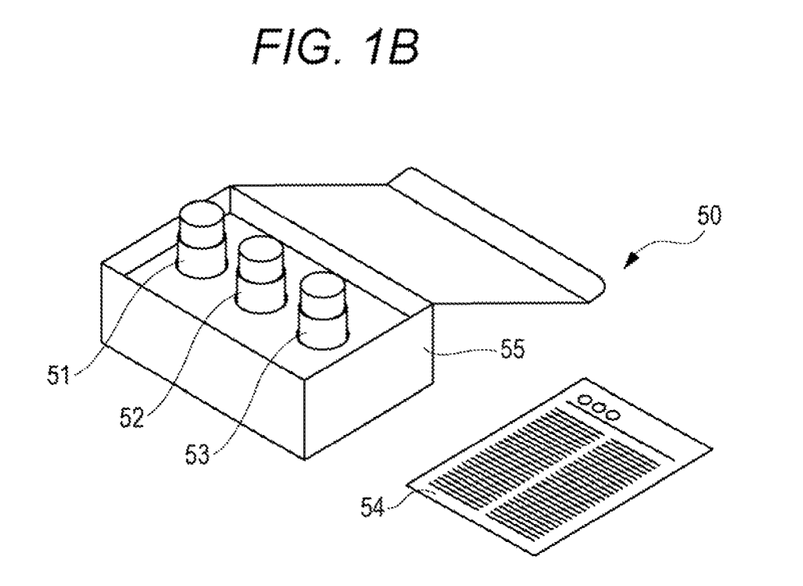
FIG. 1B is a view showing an outline of a reagent kit.

One embodiment of the present disclosure relates to a reagent kit for use in the detection of the target substance. The reagent kit comprises at least an alcohol having 1 to 7 carbon atoms, WFA, and a detection substance. FIG. 1(B) shows an example of an outline of a reagent kit. A reagent kit 50 shown in FIG. 1(B) includes an outer box 55, a first container 51 storing the reagent comprising an alcohol having 1 to 7 carbon atoms described in the above 2. (1), a second container 52 storing the reagent comprising WFA immobilized on the carrier described in the above 1, a third container 53 storing a reagent comprising a detection substance capable of binding to the target substance described in the above 1, and an attached document 54 of the reagent kit. In the attached document 54, a handling method of the reagent kit, storage conditions, expiration date, etc. can be described.

When the alcohol having 1 to 7 carbon atoms is contained in the reagent comprising WFA immobilized on the carrier contained in the second container 52, the first container 51 comprises a reagent comprising the aqueous solvent described in the above 2. (1) and at least one selected from the group consisting of additives and metal salts as necessary.

When the alcohol having 1 to 7 carbon atoms is contained in the reagent contained in the first container 51, the WFA immobilized on the carrier contained in the second container 52 may be in a dry form. In addition, when the WFA included in the reagent kit is not immobilized on the carrier at the time of distribution, a reagent for immobilizing the WFA on the carrier, the WFA and the carrier may be individually packed before use.

Examples of the reagent contained in the third container 53, for example, when the target substance is M2BP, include a HISCL (trademark) M2BPGi (trademark) R3 reagent manufactured by Sysmex Corporation. Also, when detecting another target substance, an anti-M2BP antibody contained in the HISCL (trademark) M2BPGi (trademark) R3 reagent can be changed according to the substance that specifically binds to the target substance.

Further, in the reagent kit, a container comprising a diluent for diluting a sample (for example, a HISCL (trademark) R4 reagent manufactured by Sysmex Corporation), a container comprising a substrate reagent (for example, a R5 reagent for HISCL (trademark) manufactured by Sysmex Corporation), a container comprising an aqueous medium for washing and the like may be packed together in the outer box 55.

Note that the description of the terms described in the above 1 is incorporated in this section.

EXAMPLES

1. Reagents, Specimen, and Measurement (1-1) Buffer Solution for Sample Dilution (First Reagent)
A HISCL (trademark) M2BPGi R1 reagent manufactured by Sysmex Corporation was used.
(1-2) Magnetic Particles on which WFA Lectin is Immobilized (Second Reagent)
For a system using M2BP and MUC1 as target substances, a HISCL (trademark) M2BPGi R2 reagent manufactured by Sysmex Corporation was used.

(1-2') Magnetic Particles on which LTL Lectin is Immobilized (Second Reagent)
(1-2'-1) Biotinylation of LTL Lectin LTL [manufactured by VECTOR Laboratories, trade name: Lotus tetragonolobus Lectin] was added to a 20 mM phosphate buffer solution (pH 7.5) so that the concentration of the LTL was 2.5 mg/mL to obtain a LTL-containing solution.

5-(N-Succinimidyloxycarbonyl)pentyl D-biotinamide (manufactured by DOJINDO LABORATORIES, trade name: Biotin-ACS-Osu) which is a crosslinking agent comprising biotin was added to the obtained LTL-containing solution so that the LTL/crosslinking agent (molar ratio) would be 1/100. The resulting solution was incubated at 25° C. for 90 minutes to react the LTL lectin with the crosslinking agent comprising biotin to obtain a reaction product.

(1-2'-2) Purification of Biotinylated LTL

The reaction product obtained in (1-2'-1) was purified by high performance liquid chromatography under the following conditions to obtain a purified biotinylated LTL.

Elution solvent: phosphate buffer solution (pH 6.5)
Separation column: gel filtration column (1-2'-3) Preparation of Streptavidin-Bound Particle-Containing Liquid The complex (amount of streptavidin (STA) per 1 g of magnetic particles: 2.9 to 3.5 mg; hereinafter, also referred to as "STA-bound magnetic particles") in which streptavidin was immobilized on the surface of the magnetic particles (average particle diameter 2 μm) was washed three times with a 0.01 M HEPES buffer solution (pH 7.5). The washed STA-bound magnetic particles were added to a 0.01 M HEPES buffer solution (pH 7.5) so as to have a STA concentration of 18 to 22 μg/ml (a concentration of STA-bound magnetic particles of 0.48 to 0.52 mg/mL) to obtain an STA-bound particle-containing liquid.

(1-2'-4) Preparation of LTL Immobilized Carrier

The biotinylated LTL was added to the STA-bound particle-containing liquid obtained so that the concentration of the biotinylated LTL was 20 μg/mL, and streptavidin of the STA-bound magnetic particles was bound to biotin of the biotinylated LTL. The resulting product was washed three times with a 0.1 M MES buffer solution (pH 6.5) to obtain a LTL immobilized carrier. The resulting LTL immobilized carrier was suspended in a MES buffer solution to obtain a LTL immobilized carrier-containing solution.

(1-3) Solution Comprising Labeled M2BP Antibody (Third Reagent)

For a system using M2BP as a target substance, a HISCL (trademark) M2BPGi (trademark) R3 reagent manufactured by Sysmex Corporation was used.

(1-3') Solution Comprising Labeled MUC1 Antibody (Third Reagent)

MY.1E12 (Journal of Immunological Methods Volume 270, Issue 2, 15 Dec. 2002, Pages 199-209) was used as a MUC1 antibody. The MUC1 antibody was dissolved in a phosphate buffer solution and EDTA concentration of the resulting solution was adjusted to 1 mM. An appropriate amount of a 2-mercaptoethylamine hydrochloride solution was added to the antibody solution, and the mixture was reacted at 37° C. for a predetermined time. Thereafter, the antibody solution was desalted using a PD-10 column (GE Healthcare Japan) and adjusted to a predetermined concentration.

A maleimide crosslinking agent as an ALP labeling agent was dissolved in N,N-dimethylformamide (DMF) to prepare a maleimide crosslinking agent solution. An appropriate amount of the maleimide crosslinking agent solution was added to the ALP solution, and the mixed solution was placed at 37° C. for a predetermined time to introduce a maleimide group. Thereafter, the solution was desalted using a PD-10 column (GE Healthcare Japan) and adjusted to a predetermined concentration.

The antibody solution and the ALP solution were mixed at a predetermined ratio, and the mixed solution was put in a refrigerator to cause a coupling reaction. Thereafter, a 2-mercaptoethylamine hydrochloride solution was added to stop the reaction. The ALP antibody solution was gel-filtered, and a desired fraction was collected.

The resulting desired fraction was dissolved at a predetermined concentration in a buffer solution comprising BSA, and used as a third reagent of a labeled MUC1 antibody.

(1-3") Solution Comprising Labeled Haptoglobin Antibody (Third Reagent)

The labeled haptoglobin antibody was obtained from ABCAM (manufacturer catalog number: AB13429), labeled in the same manner as 1-3', and used as a third reagent of the labeled haptoglobin antibody.

(1-4) Buffer Solution for Measurement (Fourth Reagent)

A HISCL (trademark) R4 reagent manufactured by Sysmex Corporation was used.

(1-5) Substrate (Fifth Reagent)

A HISCL (trademark) R5 reagent (manufactured by Sysmex Corporation) using CDP-Star (trademark) (Applied Biosystems) as a chemiluminescent substrate of alkaline phosphatase was used as a fifth reagent.

(1-6) Specimen

As measurement specimens, a stock solution of human serum and diluted serum obtained by diluting the human serum two times, four times, and eight times with a HISCL (trademark) specimen diluent were used.

2. Example 1

Influence of addition of glycerol on dilution linearity was studied.

M2BP was measured with a fully automated immunoassay system HISCL (trademark) 5000 (manufactured by Sysmex Corporation) using the first to fifth reagents described above. In the measurement, glycerol was added to the HISCL (trademark) M2BPGi (trademark) R1 reagent so as to be 15 w/w %. 100 μl of the R1 reagent, 30 μl of the R2 reagent, and 10 μl of the measurement specimen were mixed, and incubated according to setting of the apparatus, then B/F separation was performed, and the R3 reagent was added to obtain a measured value (luminescence intensity).

Based on the measurement results, a correlation coefficient ($R^2$ value) between the theoretical regression line obtained from the dilution factor and the actual measurement result was obtained.

Figure 2:
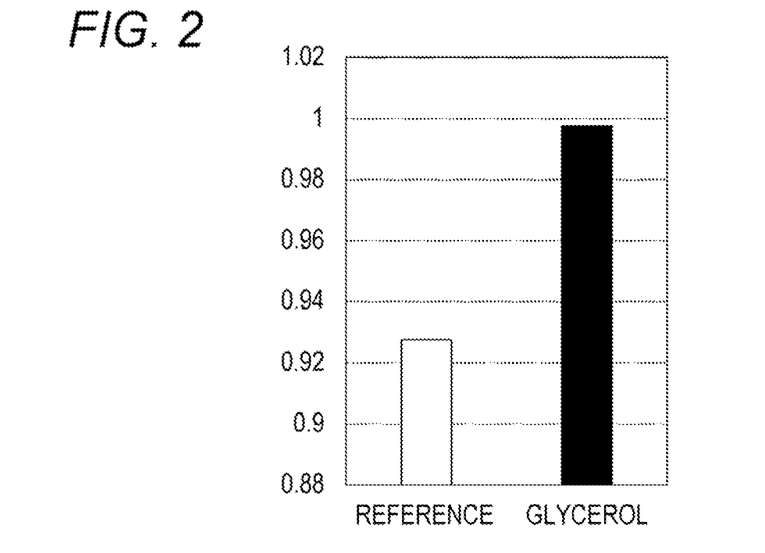
FIG. 2 shows dilution linearity when glycerol was added to a detection system.

As shown in FIG. 2, as compared with Reference (without addition), the detection system to which glycerol was added showed a good $R^2$ value, and showed a clear improvement in specimen dilution linearity.

3. Example 2

Figure 3:
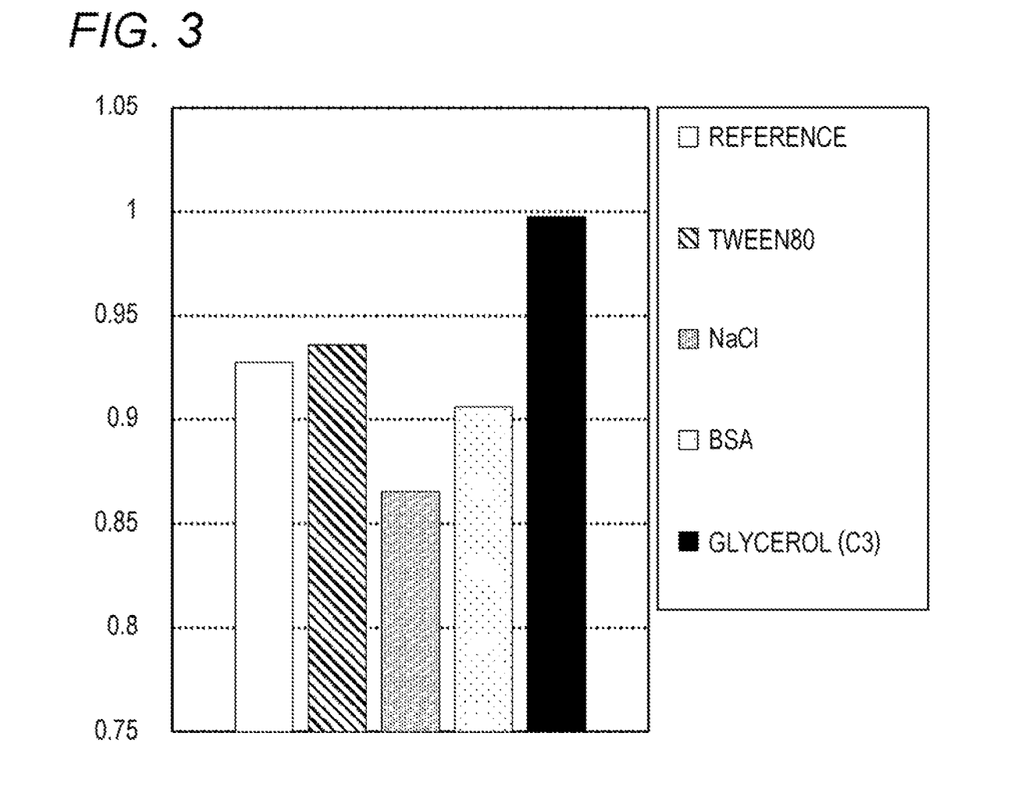
FIG. 3 shows dilution linearity when a substance other than alcohol was added to a detection system.

Influence of addition of glycerol and other substances on dilution linearity was studied. Tween 80, NaCl, bovine serum albumin (BSA) or glycerol was added to the HISCL (trademark) M2BPGi (trademark) R1 reagent so as to be 15 w/w %, and dilution linearity of M2BP measurement was examined in the same manner as in Example 1. As shown in FIG. 3, as compared with Reference (without addition), only glycerol showed a good $R^2$ value as compared with the case where other substances were added, and showed a clear improvement in specimen dilution linearity.

4. Example 3

Figure 4:
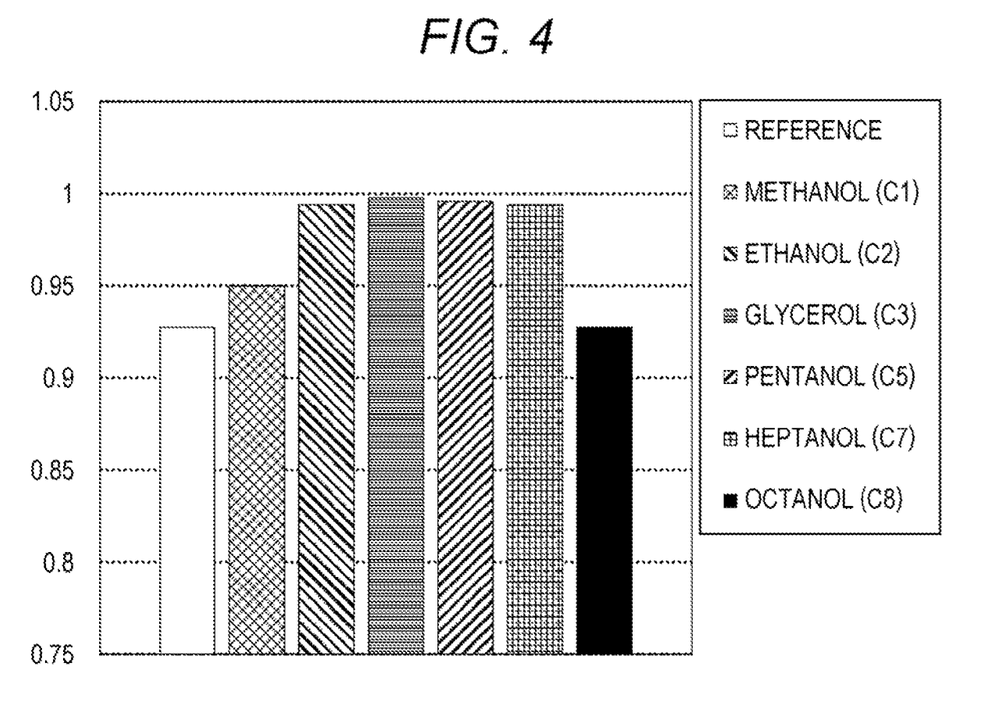
FIG. 4 shows dilution linearity when alcohols having various carbon numbers were added to a detection system.

Next, methanol (C1), ethanol (C2), glycerol (C3), pentanol (C5), heptanol (C7) and octanol (C8) having different carbon numbers were added to the HISCL (trademark) M2BPGi (trademark) R1 reagent so as to be 15 w/w %, and influence on the specimen dilution linearity of M2BP measurement was confirmed. The measurement was performed in the same manner as in Example 1. As shown in FIG. 4, in alcohols having 1 to 7 carbon atoms, particularly having 2 to 7 carbon atoms, improvement in specimen dilution linearity was shown. On the other hand, even when octanol having 8 carbon atoms was added, improvement in specimen dilution linearity was not observed.

5. Example 4

Dilution linearity of a specimen was confirmed by changing the lectin and the target substance. WFA or Lotus tetragonolobus Lectin (LTL) was used as the lectin. As the target substance, M2BP, MUC1 or haptoglobin was used. In a system using LTL, magnetic particles on which the LTL lectin described in (1-2') was immobilized were used as the second reagent. When measuring MUC1, a solution comprising the labeled MUC1 antibody described in (1-3') was used as the third reagent. When measuring haptoglobin, the labeled haptoglobin antibody described in (1-3") was used as the third reagent. In all detection systems, the HISCL (trademark) M2BPGi (trademark) R1 reagent was used as the first reagent, and glycerol was added to the first reagent in the same manner as in Example 1. The measurement was performed in the same manner as in Example 1.

Figure 5:
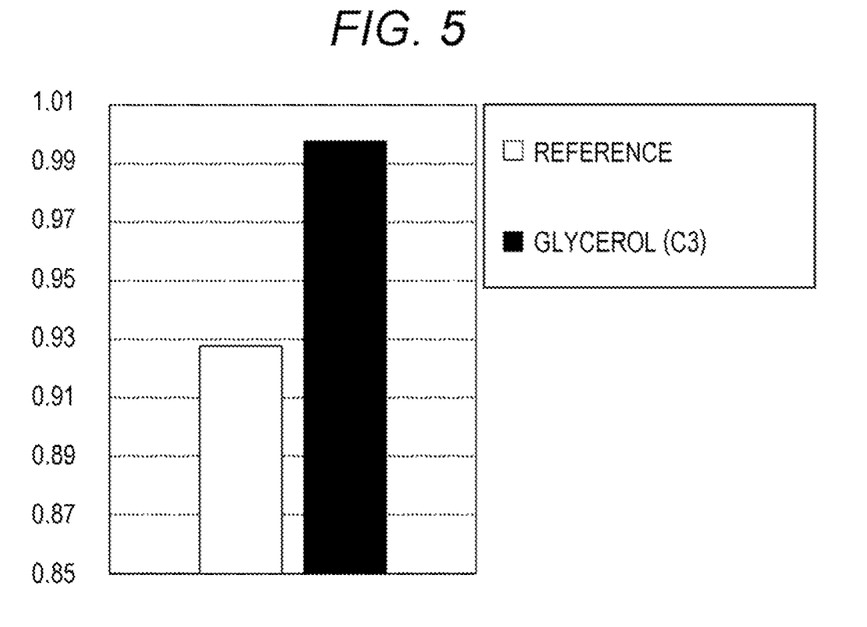
FIG. 5 shows dilution linearity of a specimen of a WFA-M2BP detection system when glycerol was added.
Figure 6:
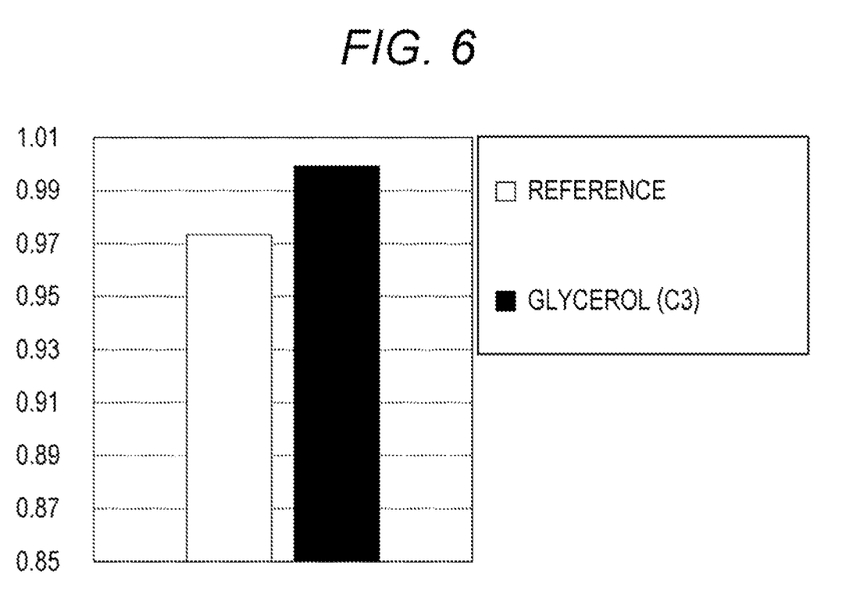
FIG. 6 shows dilution linearity of a WFA-MUC1 detection system when glycerol was added.
Figure 7:
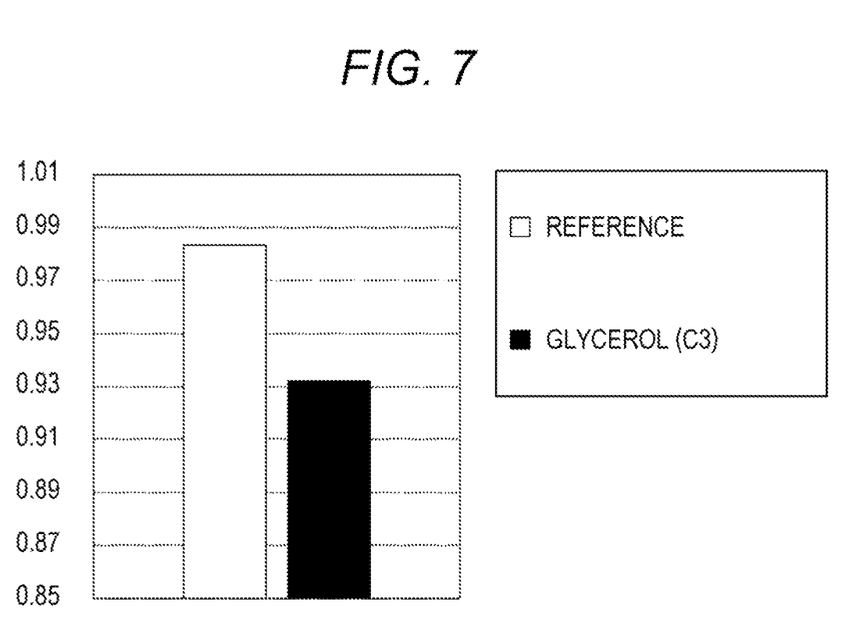
FIG. 7 shows dilution linearity of a LTL-haptoglobin detection system when glycerol was added.

The results are shown in FIGS. 5 to 7. The detection systems using WFA as the lectin (FIGS. 5 and 6) showed improvement in specimen dilution linearity by adding glycerol regardless of the target substances (M2BP and MUC1). On the other hand, in the detection system of haptoglobin using LTL as the lectin (FIG. 7), the specimen dilution linearity was reduced by adding glycerol.

Therefore, it was shown that addition of alcohol is useful for the detection system using WFA although no target substance is selected.

6. Example 5

Figure 8:
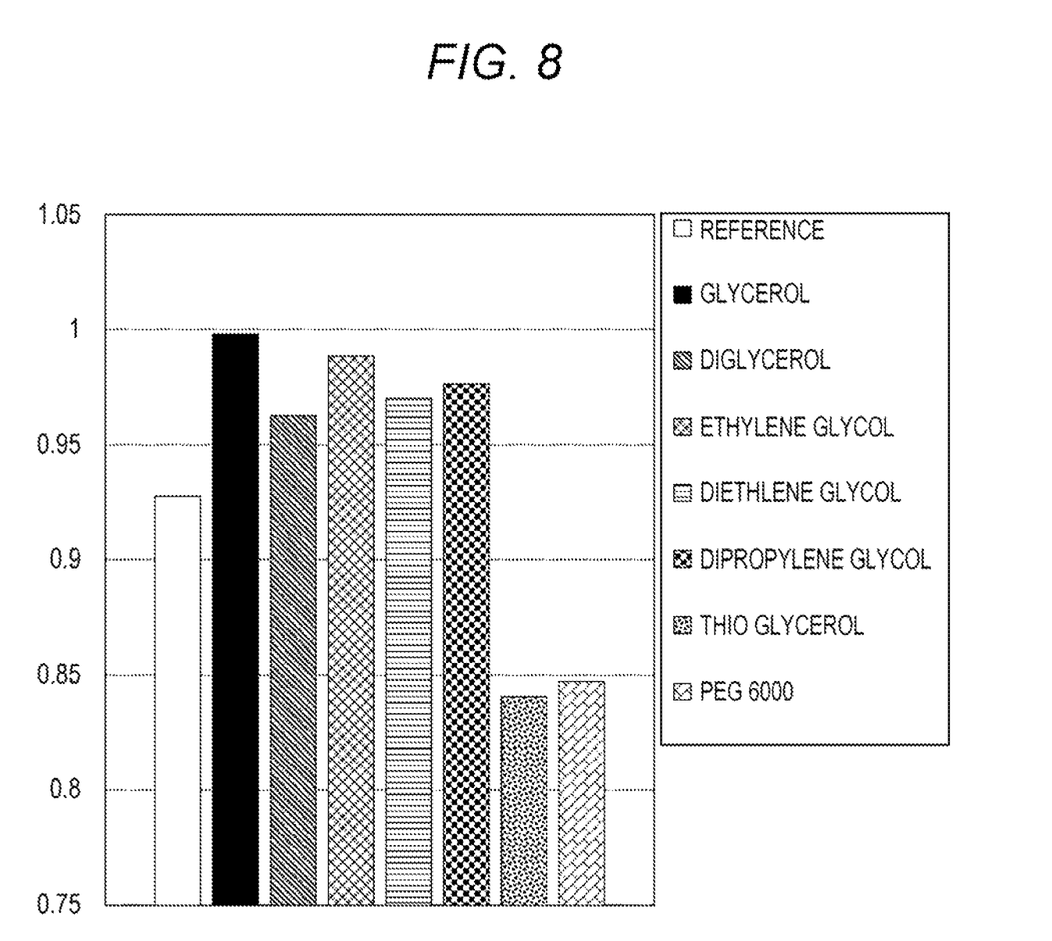
FIG. 8 shows dilution linearity when a glycerol compound was added to a detection system.

In order to confirm an effect of other alcohols, diglycerol, ethylene glycol, diethylene glycol, dipropylene glycol and PEG6000 were added in addition to glycerol, and the specimen dilution linearity was examined using M2BP as the target substance. Furthermore, the reducing agent (thioglycerol) used in the treatment for suppressing non-specific binding of the labeled lectin in US 2017/0,122,940 A was added, and performance thereof was compared with that of glycerol. Each additive was added to the first reagent, and the measurement was performed in the same manner as in Example 1. As shown in FIG. 8, the specimen dilution linearity was also improved with diglycerol, ethylene glycol, diethylene glycol, and dipropylene glycol. On the other hand, when PEG6000 as a polymeric glycerol was added, the specimen dilution linearity was conversely significantly reduced. In addition, when thioglycerol was added, performance of specimen dilution linearity was significantly reduced.

From the above results, it became clear that improvement in specimen dilution linearity was observed even when another glycerol compound was added as an alcohol having 3 to 6 carbon atoms.

7. Example 6

Figure 9:
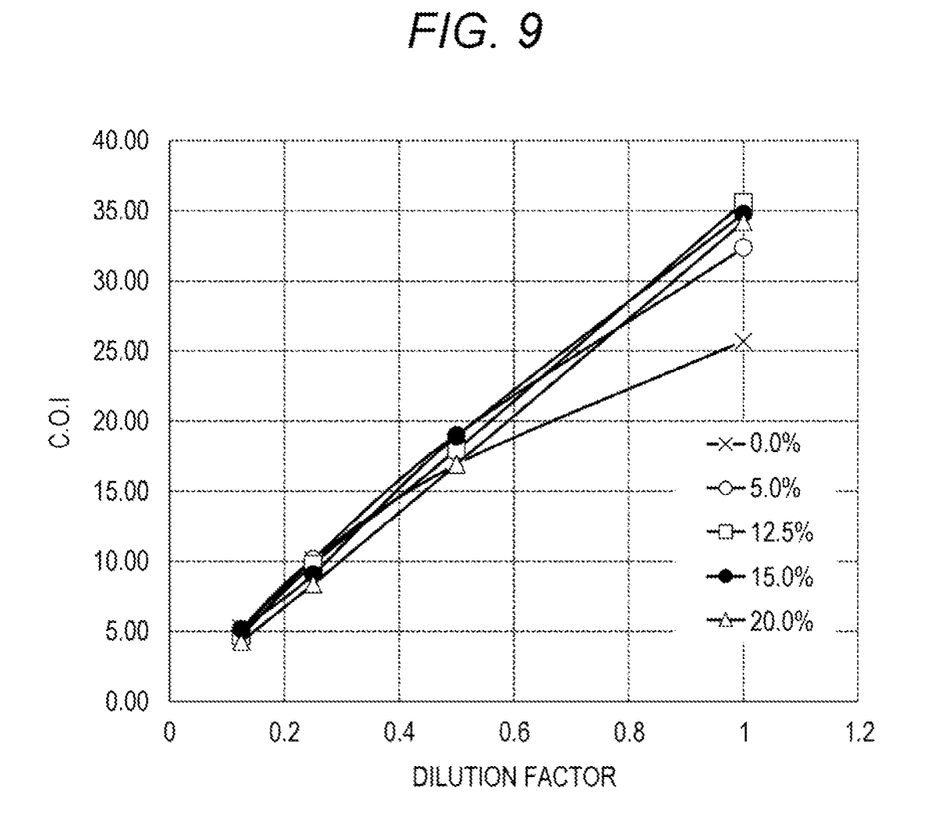
FIG. 9 shows dilution linearity when various concentrations of glycerol were added to a detection system.

Next, the glycerol concentration added to the R1 reagent was changed to 0 w/w %, 5.0 w/w %, 12.5 w/w %, 15.0 w/w %, and 20.0 w/w %, and the specimen dilution linearity when the target substance was M2BP was examined. Each additive was added to the first reagent, and the measurement was performed in the same manner as in Example 1. As shown in FIG. 9, the specimen dilution linearity was improved at any concentration of 5.0 w/w %, 12.5 w/w %, 15.0 w/w %, and 20.0 w/w %.

From the above results, it was confirmed that addition of an alcohol having 1 to 7 carbon atoms to the detection system using WFA improves the dilution linearity of the specimen. In addition, it was considered that improvement of the inspection accuracy can be expected since the dilution linearity of the specimen is improved.

What is claimed is:

1. A method for detecting a target substance, comprising:
    forming on a carrier a complex comprising Wisteria floribunda lectin (WFA) and a target substance by mixing the WFA immobilized on the carrier with the target substance comprising a sugar chain that binds to the WFA in the presence of an alcohol; and
    detecting the target substance by detecting the complex,
    wherein the alcohol is at least one alcohol selected from the group consisting of methanol, ethanol, glycerol, pentanol, heptanol, diglycerol, ethylene glycol, diethylene glycol, propylene glycol, dipropylene glycol, triethylene glycol, and mixtures thereof.

2. The detection method according to claim 1, wherein in the formation step, the WFA, the target substance, and a detection substance that binds to the target substance and has a labeling substance are mixed in the presence of the alcohol to form a complex comprising the WFA, the target substance, and the detection substance, and
    in the detection step, the complex is detected based on the labeling substance of the complex.

3. The detection method according to claim 1, wherein in the formation step, the complex is formed in the presence of alcohol at a concentration of 2 to 20w/w %.

4. The detection method according to claim 1, wherein the target substance is a glycoprotein.

5. The detection method according to claim 1, wherein the target substance is Mac-2-binding protein (M2BP), Mucin 1, cell surface associated (MUC1), α1 acid glycoprotein (AGP), nerve cell adhesion molecule L1 (L1CAM), or KL-6 antigen.

6. The detection method according to claim 1, wherein a detection substance is an antibody that specifically binds to the target substance.

7. The detection method according to claim 1, wherein a labeling substance is at least one selected from the group consisting of a hapten, an enzyme, and a fluorescent substance.

8. The detection method according to claim 1, wherein the carrier is a particle.

9. The detection method according to claim 1, wherein in the detection step, the target substance is quantified.

* * * * *